(12) United States Patent
Aman et al.

(10) Patent No.: US 10,299,804 B2
(45) Date of Patent: May 28, 2019

(54) DUAL SPEED MEDICAL PROCEDURE POWER TOOL

(71) Applicants: Peter M Aman, Austin, TX (US); Richard Acevedo, Austin, TX (US)

(72) Inventors: Peter M Aman, Austin, TX (US); Richard Acevedo, Austin, TX (US)

(73) Assignee: INSURGICAL, INC., Austin, TX (US)

( * ) Notice: Subject to any disclaimer, the term of this patent is extended or adjusted under 35 U.S.C. 154(b) by 525 days.

(21) Appl. No.: 15/090,618

(22) Filed: Apr. 4, 2016

(65) Prior Publication Data

US 2016/0345985 A1    Dec. 1, 2016

Related U.S. Application Data (60) Provisional application No. 62/168,834, filed on May 31, 2015.

(51) Int. Cl.
    *A61B 17/00*      (2006.01)
    *A61B 17/16*      (2006.01)
    *A61B 17/14*      (2006.01)

(52) U.S. Cl.
    CPC ........ *A61B 17/1622* (2013.01); *A61B 17/142* (2016.11); *A61B 17/144* (2016.11); *A61B 17/162* (2013.01); *A61B 17/1626* (2013.01); *A61B 17/1624* (2013.01); *A61B 2017/00393* (2013.01); *A61B 2017/00734* (2013.01)

(58) Field of Classification Search
CPC combination set(s) only.
See application file for complete search history.

(56) References Cited

U.S. PATENT DOCUMENTS

| | | |
|---|---|---|
| 2011/0196375 A1 | 8/2011 | Li |
| 2016/0144529 A1* | 5/2016 | Barnett ............... B27B 17/08 30/381 |

FOREIGN PATENT DOCUMENTS

| | | |
|---|---|---|
| CN | 101045006 A | 10/2007 |
| DE | 3311263 A1 | 10/1984 |
| EP | 0238204 A1 | 9/1987 |
| EP | 1109507 A1 | 3/2000 |
| GB | 772210 | 4/1957 |
| GB | 1470447 A | 11/1974 |

\* cited by examiner

*Primary Examiner* — Sameh R Boles
(74) *Attorney, Agent, or Firm* — Clearpat Services, LLC (57) ABSTRACT

A dual speed medical procedure power tool includes first and second gear sets. The first and second gear sets may be engaged and disengaged, selectively, to provide a first speed for a high-speed, low-torque drilling function and a second speed for a low-speed, high-torque reaming function.

22 Claims, 6 Drawing Sheets

DUAL SPEED MEDICAL PROCEDURE POWER TOOL

CROSS REFERENCE TO RELATED APPLICATION

The present application is related to and claims priority to U.S. Provisional Application No. 62/168,834 filed on May 31, 2015.

BACKGROUND

This disclosure relates generally to single use or limited use power tools and more particularly to external components that can be removed for cleaning when a tool is being cleaned, reconditioned, sterilized and deployed for re-use.

Important factors for any surgical instrument include sterility, cost of acquisition, maintenance, and reliability during use in the surgical suite. Each of these factors can have a significant impact on the cost of medical care for both the patient and the provider.

In recent years, there has been significant focus on the ever increasing cost of medical care. These cost increases have led to skyrocketing insurance premiums, reduced coverage, reduced reimbursements, increased fees for services, severe reductions in the services for some patient groups by some providers, and unfortunately an apparent increase in infections and medical mishaps.

In an effort to reduce costs and improve profitability, both service providers and medical device suppliers are continuously looking for ways to streamline procedures, reduce time, cost, and risk from their products and services without reducing the quality of the products or services they provide to their customers. One area to benefit from these savings and improvements has been in the orthopedic surgical field through the use of high precision, battery powered surgical instrumentation. In the late 1960's and early 1970's battery operated drills were bulky, ill-balanced and required multiple batteries to perform some surgeries due to the limited energy storage capacity and poor efficiency of the electric motors.

Since then, manufacturers have attempted to make batteries more efficient with higher energy storage capacity, reduced size, and improved rechargeable lifespans. Likewise, motor housings such as saw and drill bodies have become more ergonomic, balanced, lightweight and energy efficient. As with many standard hand tools having multiple moving components, instrument manufacturers have reduced weight by utilizing lighter materials such as plastic housings, and gears, and put weight-reducing apertures in what were previously solid housings. In some cases, standard mountings for attachments have been replaced with modular fittings, allowing for greater interchangeability and component selections. Additionally, manufacturers have attempted to improve electrical components by upgrading them with more modern components wherever possible.

All of these improvements in equipment have improved efficiencies, costs and quality in some areas while at the same time increasing costs for acquisition, maintenance and increasing patient risks in other ways that were not previously seen or predicted. Often times cost, quality and risk can be inversely proportional to one another. One example of the increased cost and reduced patient risk is seen in the cleaning and maintenance of instruments.

Recent published reports suggest that many of the surgical instruments used in operations were not being cleaned and/or sterilized appropriately in the very hospital facilities that were established and tasked for that purpose. In numerous reports, following cleaning and sterilization, it was noted that upon closer secondary inspection, the inside of small diameter cannulas and intricate mini-components of arthroscopic shavers that are used for many of today's minimally invasive procedures, contained human tissue and bone fragments from previous surgeries. In other cases, modular components of drills and saws such as chucks, drill bits and blades were found to have similar debris or pieces of cleaning brushes and/or bristles embedded in or on them. These investigations have demonstrated that in most cases the instruments were not cleaned according to manufacturer's specifications which has likely led to many documented cases of serious, multiple, serial infections for subsequent patients. A pilot program conducted by the Centers for Medicare and Medicaid Services (Schaefer et al., 2010; JAMA 2010; 303(22): 2273-2279) inspected 1500 outpatient surgery centers and found that 28% had been cited for infectious control deficiencies associated with equipment cleaning and sterilization. The costs to the patients and the hospitals in both expense and liability to deal with these infections can be and has been staggering.

In other cases, critical battery-operated, motorized tools such as drills or bone saws have ceased to function due to dead batteries that no longer maintain their capacity to hold a charge, or due to internal part failure, often attributable to overuse or lack of proper maintenance. The resultant downtime in the operating suite is extremely costly, as the procedure step must be put on hold while replacement or substitute tools are obtained. Wait times may often exceed 20-30 minutes, resulting in additional anesthesia exposure for the patient, additional operating room time (charged to the patient) and potential delays to other procedures where the replacement or substitute equipment had been scheduled for use in a later procedure. Recent estimates (2005) establish the average cost of operating room time to range between $62/min. (range $21.80-$133.12) depending on the procedure. These figures did not include extra resources provided by the hospital for special, non-routine situations which often occur during standard procedures, and did not include the surgeon and anesthesia provider fees, (anesthesia fees are estimated to be $4/min; range $2.20-$6.10).

Hospitals and instrument manufacturers are continuously attempting to find improved ways to reduce risk associated with infection in general, and more recently, specifically from improperly cleaned instruments. One approach has been to use more disposable, single-use instruments such as drills, saw blades and plastic cannulas. Additionally, many laparoscopic devices, such as surgical staplers and trocars, are designed as single use items that are intended to be immediately disposed of after use. Unfortunately, at today's acquisition costs, the total cost of ownership and benefits are not always clear for high-use battery-operated, motorized instruments such as saws, drills and reamers used in orthopedic procedures and the idea of disposable powered instruments has not been readily embraced.

A recent trend in the medical community is the reprocessing of single use medical instruments, by parties other than the original equipment manufacturer, instead of discarding them after use. During reprocessing, the medical instruments are disassembled, cleaned and sterilized. They are then reassembled for future use. However, because the medical instruments reprocessed for further use are specifically provided for use during a single procedure, the performance of the medical instruments tends to decline after reprocessing, because the components making up the medical instrument are not adapted for multiple uses and will degrade in performance when used beyond their intended life span. For example, reprocessing of the cutting devices on trocars is intended to extend these devices beyond their intended mission life, but often results in duller cutting edges on the blades because neither the materials used nor the reprocessing method can restore the device to the original manufacturing specifications. A greater force, therefore, is needed to make an initial incision, causing more trauma to the patient. In addition, the use of greater force increases the potential for error during the surgical procedure.

Most hospitals and surgery centers buy high-use, reusable motorized, pneumatic, wired or battery operated, orthopedic surgical equipment and are expected to clean, sterilize, and maintain them internally within the hospital. Unfortunately, the technicians hired to perform this work are typically not qualified or trained to perform this work adequately for the many varieties of powered instruments used. Further, manufacturers rarely provide the hospital/client with the training or diagnostic equipment necessary to evaluate or test the equipment. Often times the hospital employees responsible for cleaning and maintenance are not technicians at all, being paid slightly more than minimum wage, working at a fast pace to merely wash, count, and reload instruments into their appropriate system trays and flash sterilize them as quickly as possible, in an effort to keep the equipment in rotation in the hospital operating rooms, where higher throughput dictates profitability for the hospital or surgery center.

As a result of high throughput requirements, general maintenance is rarely done and preventative monitoring and maintenance is almost never done on this type of equipment. Hospital budgets for internal maintenance of equipment are generally geared toward high-end, multi-million dollar capital equipment such as x-ray and radiological equipment. It is generally assumed that it is faster, simpler, and more economical for the hospital to wait for hand-held instruments, such as drills, saws and reamers to fail, then, send them back to the manufacturer for repair or replacement. Additionally, it would be beneficial to provide single use or limited use surgical power tools that have two sets of gears, one of which can be engaged while the other is not and vice versa, to enable dual speed operation depending on the location of an external control lever

SUMMARY

Accordingly, one embodiment comprises a dual speed medical procedure power tool wherein first and second gear sets are selectively engageable for performing mutually exclusive drilling and reaming speeds.

DETAILED DESCRIPTION

Figure 1:
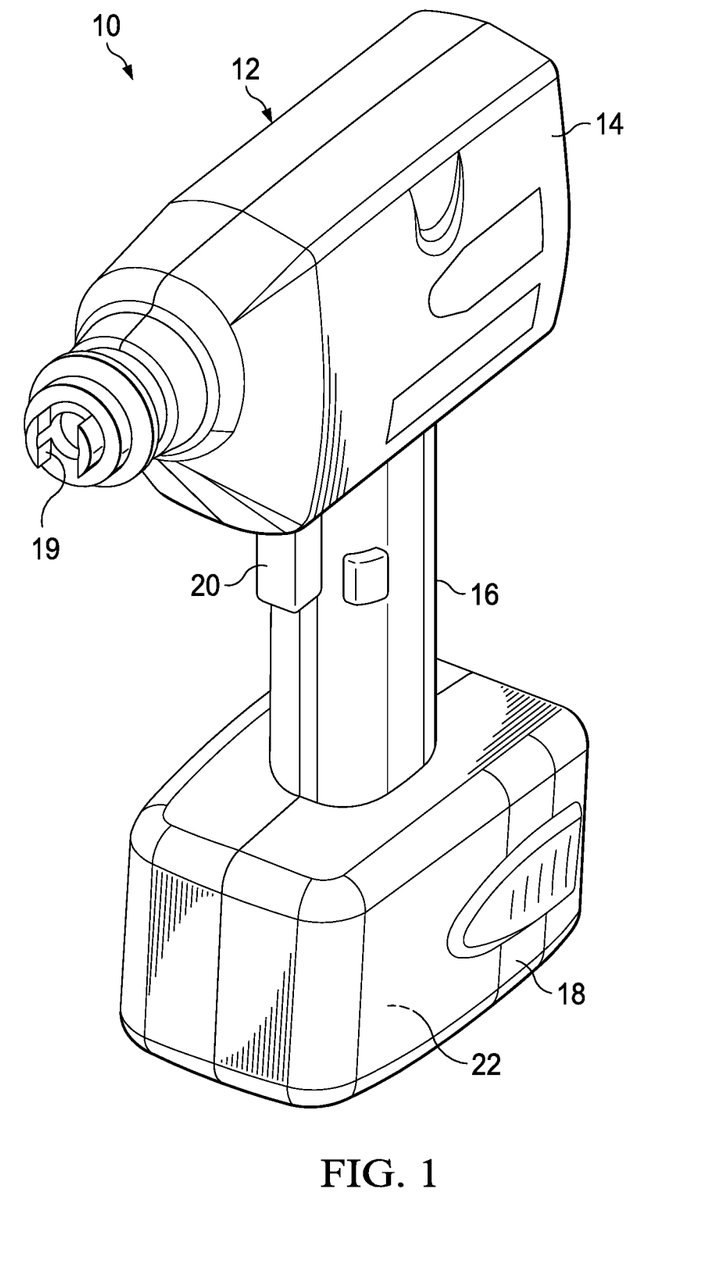
FIG. 1 is a perspective view illustrating an embodiment of a medical procedure power tool.

A medical procedure power tool 10 is illustrated in FIG. 1 and includes an integrated housing 12 having a power and attachment portion 14, a handle portion 16 and a battery-housing portion 18. The power and attachment portion 14 contains an electric motor, discussed below, and a chuck 19 for securing various attachments to the tool 10. The handle portion 16 includes a trigger 20, and the battery-housing portion 18 defines a battery compartment 22. The housing 12 is preferably formed of a synthetic material. A battery in compartment 22 may be either rechargeable or disposable.

Figure 2:
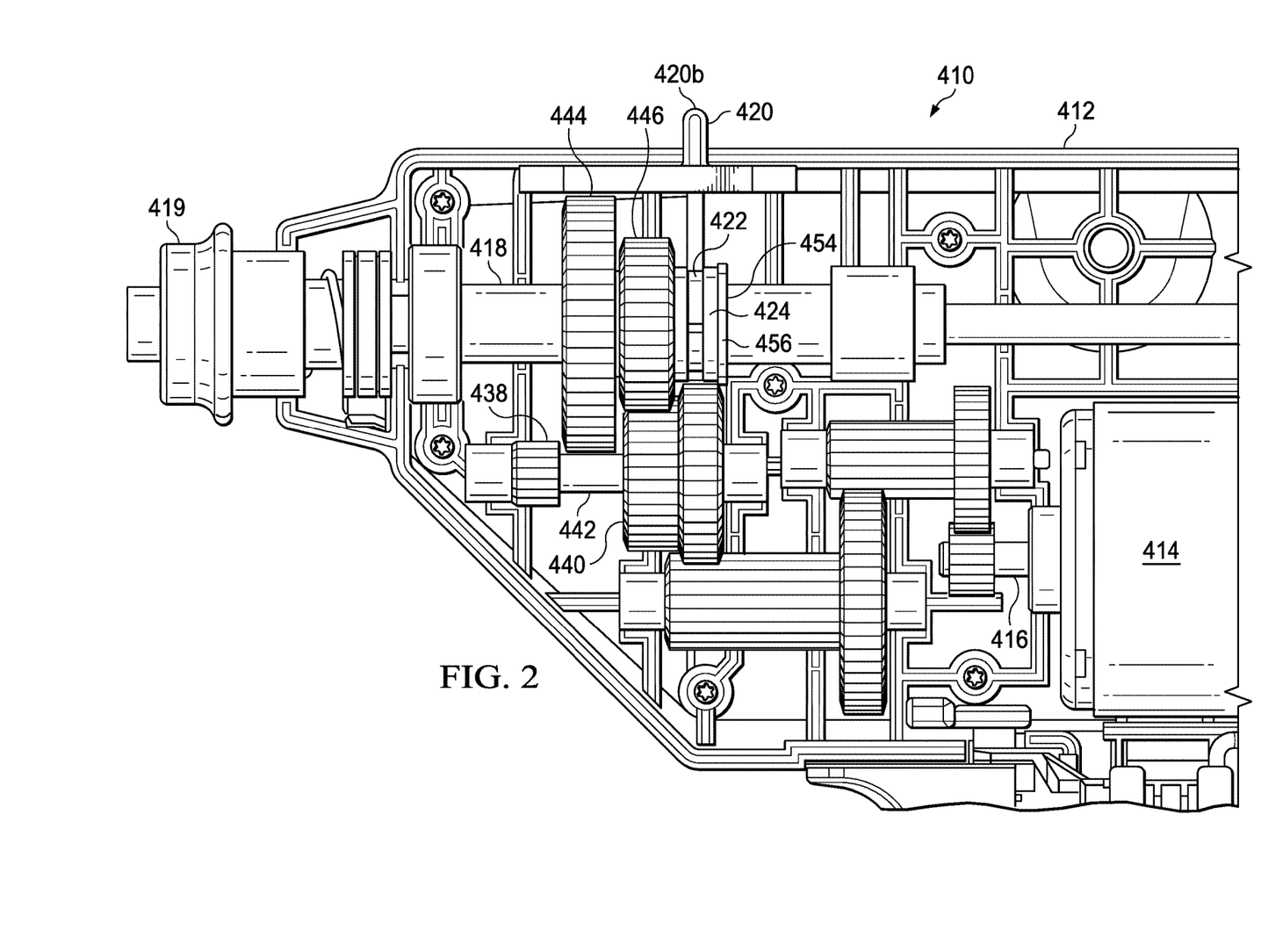
FIG. 2 is a partial cut-away side view illustrating an embodiment of a medical procedure power tool having a gear set in a first speed position.
Figure 3:
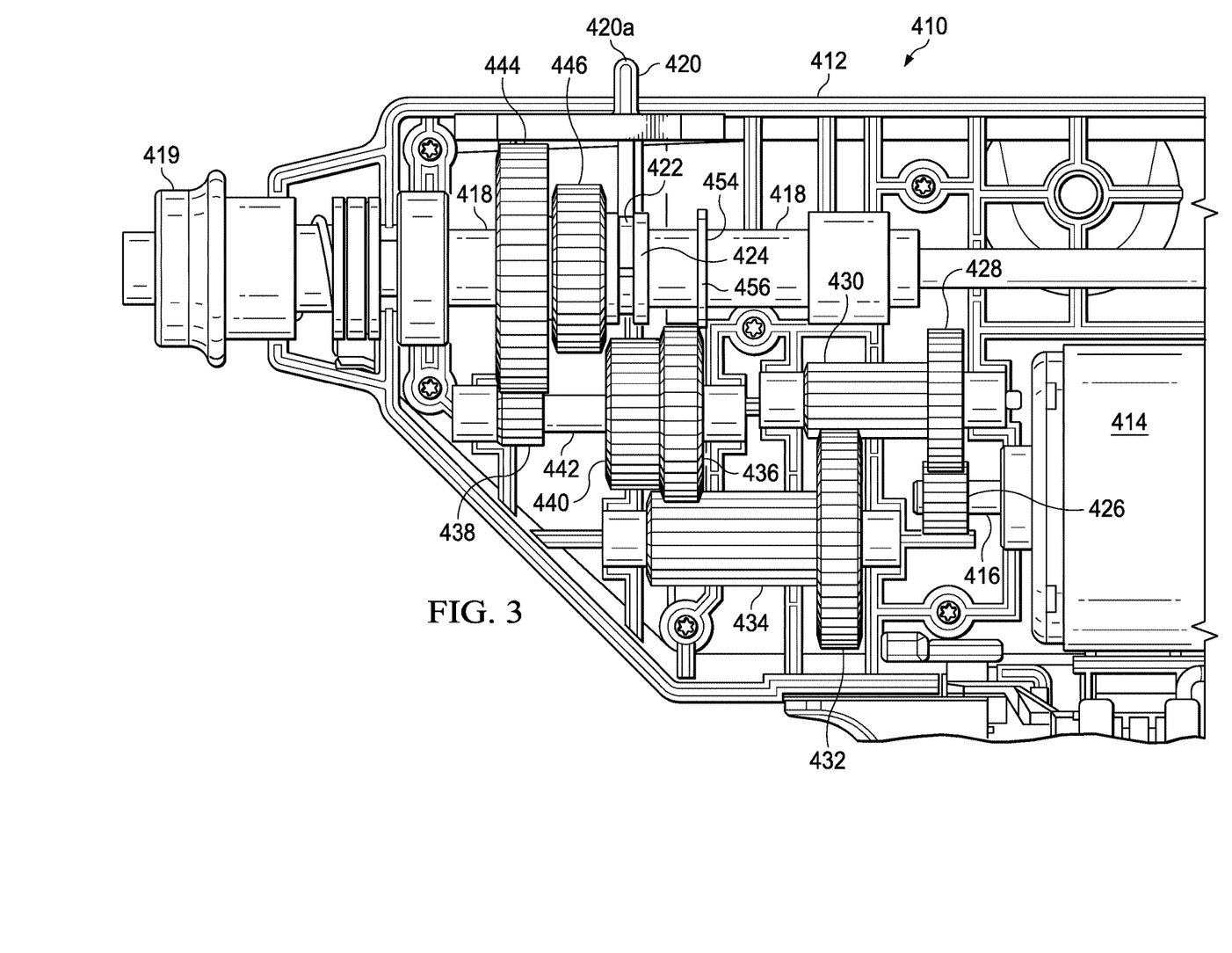
FIG. 3 is the partial cut-away view of FIG. 2 illustrating the gear set in a second speed position.

More specifically, in FIGS. 2 and 3, a medical procedure power tool 410 includes a housing 412 having a motor 414 and a motor output shaft 416. A plurality of gear clusters, discussed below, are provided to power a tool output shaft 418, and a chuck 419, at a selected speed for either a reaming or drilling operation. The tool 410 has a manually operable sliding speed selector knob 420 protruding from housing 412 and movable from a first or forward position 420a, FIG. 3, to a second or rearward position 420b, FIG. 2. A speed selector fork 422 is connected to move with selector knob 420. The fork 422 engages a receiver 424 mounted on power tool output shaft 418, see also FIGS. 4 and 5. The receiver 424 and a pair of gears, discussed below, are slidably mounted on the tool output shaft 418.

The motor 414, FIG. 3, provides rotational output via the motor output shaft 416 and through a sequential cluster of gears 426, 428, 430, 432, 434, 436 to rotationally drive a first or driving gear set including gears 438 and 440 mounted to rotate with a shaft 442. Depending on the position of speed selector knob 420, one of the gears 438 and 440 is positioned to drive a second or driven gear set including gears 444 and 446 mounted to rotate with the shaft 418. However, the gears 444 and 446 are slidably mounted on shaft 418, and simultaneously are mounted to rotate shaft 418 as further discussed below.

Figures 6, 7:
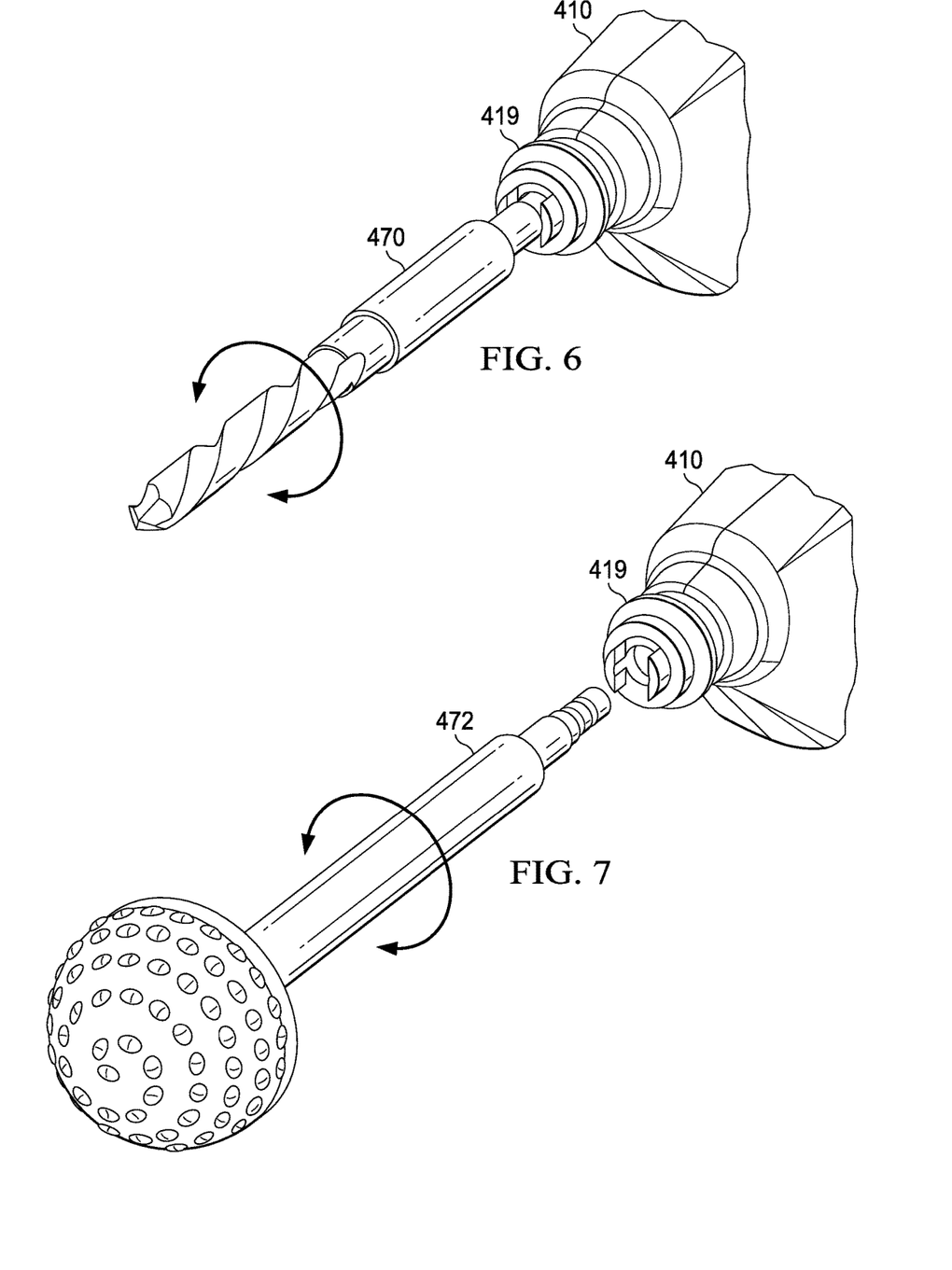
FIG. 6 is a partial view illustrating an embodiment of a drilling attachment for use with a medical procedure power tool.
FIG. 7 is a partial view illustrating an embodiment of a reaming attachment for use with a medical procedure power tool.

In operation, when it is desired to perform a drilling operation, which is a high-speed, low-torque operation, the selector knob 420 is positioned rearward, FIG. 2, thus causing the speed selector fork 422 to simultaneously move (or slide) the receiver 424 and both gears 444 and 446 rearward on shaft 418. As a result, gear 446 meshes with gear 440 and shaft 418 is rotated at the high-speed, low-torque drill setting. When it is desired to perform a reaming operation, which is a low-speed, high-torque operation, the selector knob is positioned forward, FIG. 3, causing the speed selector fork 422 to simultaneously move (or slide) the receiver 424 and both gears 444 and 446 forward on shaft 418. As a result, gear 444 meshes with gear 438 and shaft 418 is rotated at the low-speed, high-torque reaming setting. FIG. 6 illustrates an attachment 470 for use with power tool 410 to accomplish a drilling operation, and FIG. 7 illustrates an attachment 472 for use with power tool 410 to accomplish a reaming operation. Attachments 470 and 472 are bidirectionally rotatable.

Figure 4:
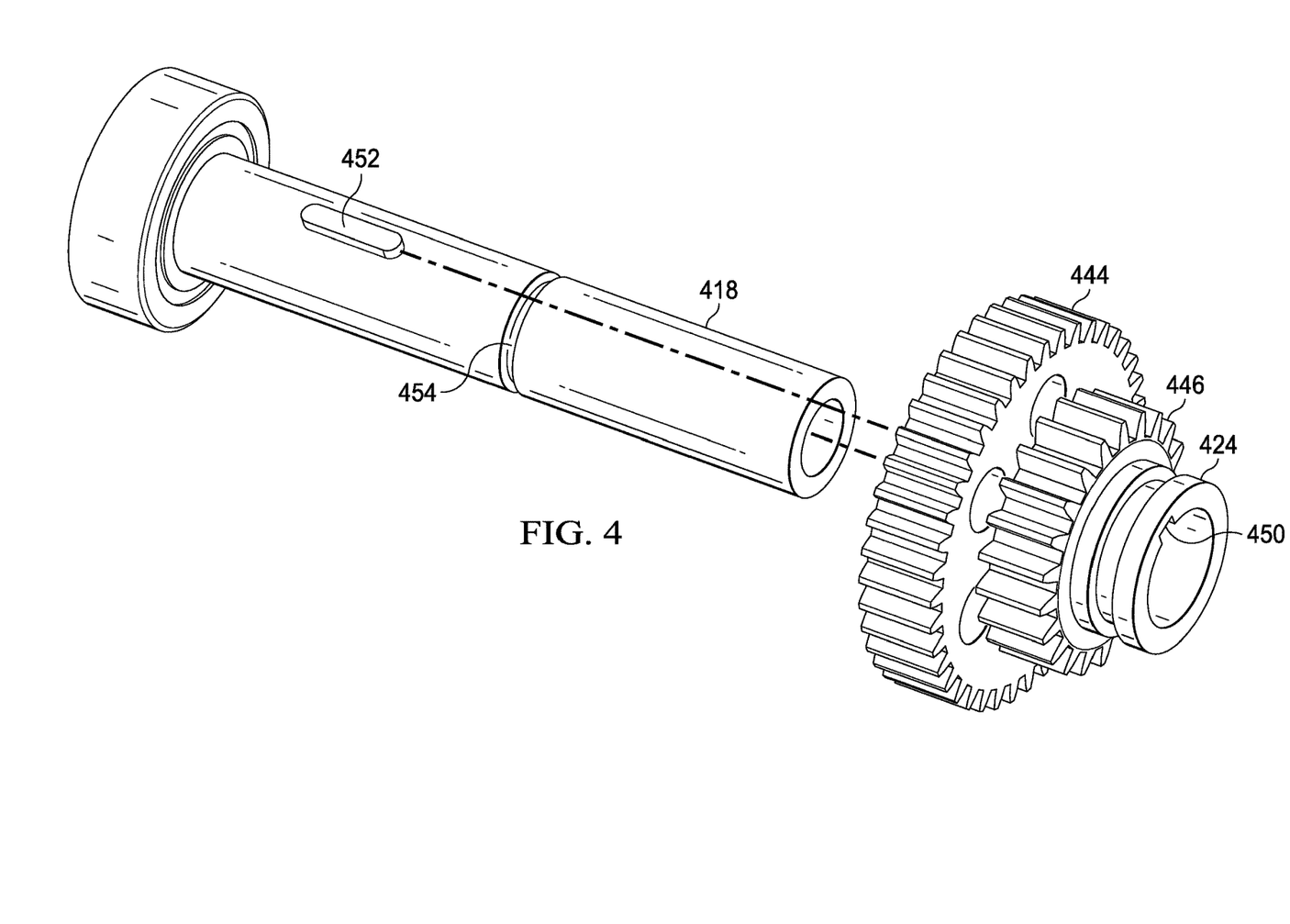
FIG. 4 is a perspective exploded view illustrating a gear set capable of axial motion on a shaft and transfer of rotational energy to the shaft.
Figure 5:
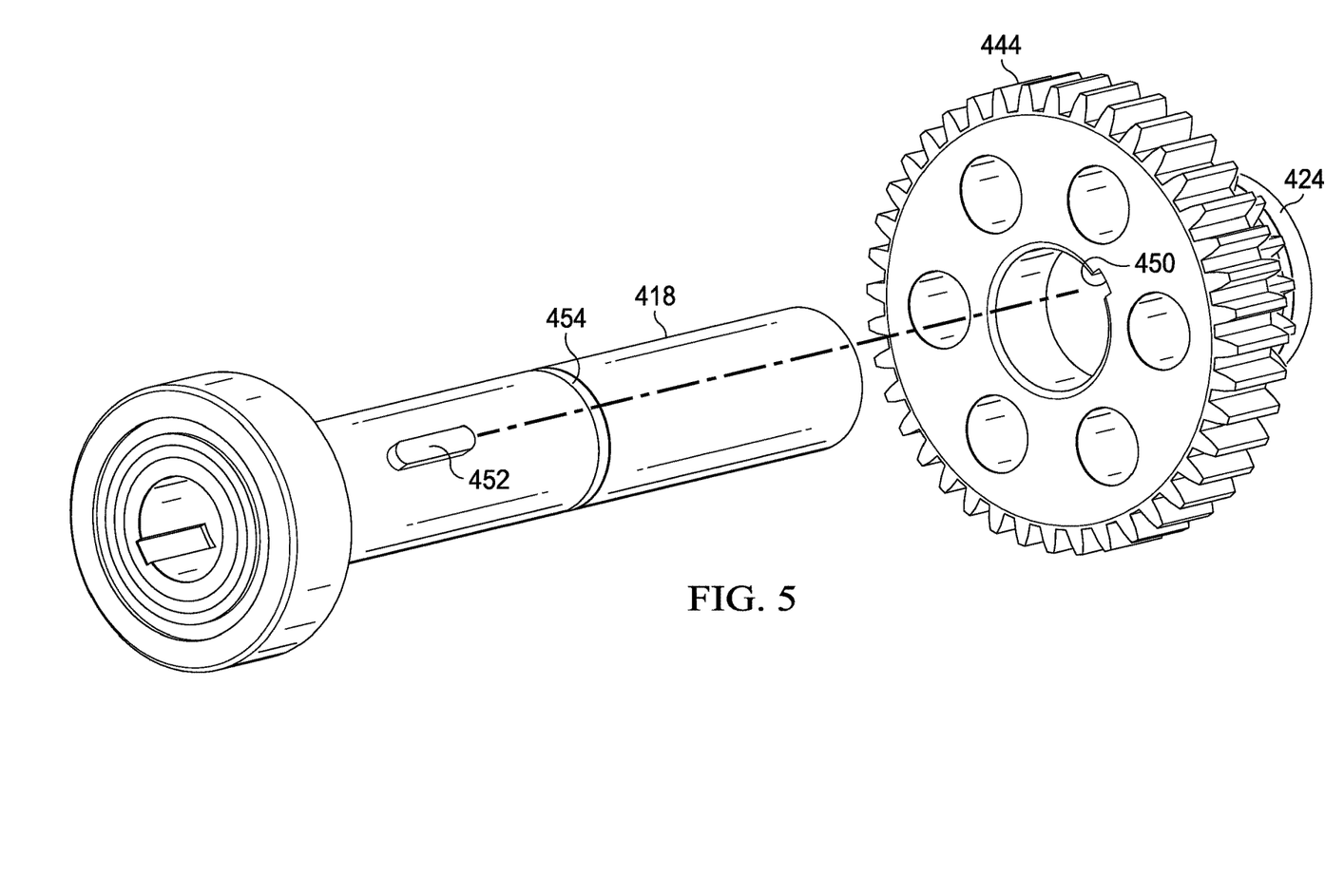
FIG. 5 is an alternate perspective view of the gear set of FIG. 4.

Gears 444 and 446 are enabled to slide on shaft 418 and also transfer rotational energy to shaft 418 and chuck 419 due to a key and keyway connection, see FIGS. 4 and 5. The gears 444, 446 and the receiver 424 have a continuous keyway 450, which engages a key 452 mounted on shaft 418. A groove 454 in shaft 418 receives a ring 456, FIGS. 2 and 3, which limits rearward sliding movement of gears 444, 446 and receiver 424 on shaft 418.

As a result of the foregoing, a dual speed medical procedure power tool 410 is provided. The power tool 410 comprises a housing 412 including a motor 414 providing a rotational output 416 to a first gear set having a first driving gear 438 and a second driving gear 440, the first and second driving gears rotating with a first shaft 442. A second gear set in the housing rotates with, and is axially movable on, a second shaft 418, the second gear set including a first driven gear 444 and a second driven gear 446, the first and second driven gears 444, 446 being selectively axially movable into and out of engagement, respectively, with the first and second driving gears 438, 440. A speed selector 420 is mounted on the housing 412 and is connected to move the axially movable gears, 444, 446 from a first position, wherein the first driving gear 438 engages the first driven gear 444, to a second position wherein the second driving gear 440 engages the second driven gear 446, whereby mutually exclusive drilling and reaming speeds are selected. It should be apparent that the same variable speed result could be achieved in an alternate embodiment, wherein a pair of driving gears could be axially positionable to engage a pair of axially stationary driven gears, which is opposite of the gear arrangement as illustrated above.

Although illustrative embodiments have been shown and described, a wide range of modification, change and substitution is contemplated in the foregoing disclosure and in some instances; some features of the embodiments may be employed without a corresponding use of other features. Accordingly, it is appropriate that the appended claims be construed broadly and in a manner consistent with the scope of the embodiments disclosed herein.

What is claimed is:

1. A dual speed medical procedure power tool comprising: a housing including a motor providing a rotational output to a first gear set having a first driving gear and a second driving gear, the first and second driving gears rotating with a first shaft; a second gear set in the housing rotating with, and axially movable on, a second shaft, the second gear set including a first driven gear and a second driven gear, the first and second driven gears being selectively axially movable into and out of engagement, respectively, with the first and second driving gears; and a speed selector mounted on the housing and connected to move the axially movable gears from a first position, wherein the first driving gear engages the first driven gear, to a second position wherein the second driving gear engages the second driven gear, whereby mutually exclusive drilling and reaming speeds are selected, wherein the first and second driven gears, and the receiver, include a continuous keyway; and a key mounted on the second shaft engages the continuous keyway.

2. The power tool of claim 1, wherein the speed selector comprises a speed selector knob protruding from the housing.

3. The power tool of claim 2, wherein the speed selector knob protrudes from the housing and is movable between a first position and a second position.

4. The power tool of claim 3, further comprising:
a speed selector fork connected to move with the speed selector knob, whereby the first and second driven gears are axially movable on the second shaft.

5. The power tool of claim 4, wherein the speed selector fork engages a receiver mounted on the second shaft.

6. The power tool of claim 2, wherein the first and second driven gears move in response to movement of the speed selector knob.

7. The power tool of claim 1, wherein the first shaft rotates a sequential cluster of gears coupled to drive the first and second driving gears.

8. A dual speed medical procedure power tool comprising: a housing including a motor providing a rotational output to a first gear set having a first driving gear and a second driving gear, the first and second driving gears rotating with a first shaft; a second gear set in the housing rotating with, and axially movable on, a second shaft, the second shaft being mounted to rotate parallel to the first shaft, the second gear set including a first driven gear and a second driven gear, the first and second driven gears being selectively axially movable into and out of engagement, respectively, with the first and second driving gears; and a speed selector mounted on the housing and connected to move the axially movable gears from a first position, wherein the first driving gear engages the first driven gear, to a second position wherein the second driving gear engages the second driven gear, whereby mutually exclusive drilling and reaming speeds are selected, wherein the first and second driven gears, and the receiver, include a continuous keyway; and a key mounted on the second shaft engages the continuous keyway.

9. The power tool of claim 8, wherein the speed selector comprises a speed selector knob protruding from the housing.

10. The power tool of claim 9, wherein the speed selector knob is movable between a first position and a second position.

11. The power tool of claim 10, further comprising:
a speed selector fork connected to move with the speed selector knob, whereby the first and second driven gears are axially movable on the second shaft.

12. The power tool of claim 11, wherein the speed selector fork engages a receiver mounted on the second shaft.

13. The power tool of claim 9, wherein the first and second driven gears move in response to movement of the speed selector knob.

14. The power tool of claim 8, wherein the first shaft rotates a sequential cluster of gears coupled to drive the first and second driving gears.

15. A dual speed medical procedure power tool comprising: a housing including a motor providing a rotational output to a first gear set having a first driving gear and a second driving gear, the first and second driving gears rotating with a first shaft, the first and second driving gears being mounted to be axially stationary on the first shaft; a second gear set in the housing rotating with, and axially movable on, a second shaft, the second gear set including a first driven gear and a second driven gear, the first and second driven gears being selectively axially movable into and out of engagement, respectively, with the first and second driving gears; and a speed selector mounted on the housing and connected to move the axially movable gears from a first position, wherein the first driving gear engages the first driven gear, to a second position wherein the second driving gear engages the second driven gear, whereby mutually exclusive drilling and reaming speeds are selected, wherein the first and second driven gears, and the receiver, include a continuous keyway; and a key mounted on the second shaft engages the continuous keyway.

16. The power tool of claim 15, wherein the speed selector comprises a speed selector knob protruding from the housing.

17. The power tool of claim 16, wherein the speed selector knob is movable between a first position and a second position.

18. The power tool of claim 17, further comprising:
a speed selector fork connected to move with the speed selector knob whereby the first and second driven gears are axially movable on the second shaft.

19. The power tool of claim 18, wherein the speed selector fork engages a receiver mounted on the second shaft.

20. The power tool of claim 16, wherein the first and second driven gears move in response to movement of the speed selector knob.

21. The power tool of claim 15, wherein the first shaft rotates a sequential cluster of gears coupled to drive the first and second driving gears.

22. A dual speed medical procedure power tool comprising: a housing including a first gear set, the first gear set mounted on and rotating with a first shaft; a second gear set in the housing rotating with, and axially movable on, a second shaft, the second gear set being selectively axially movable into and out of engagement, respectively, with the first gear set; and a speed selector mounted on the housing and connected to move the second gear set from a first position, wherein a first gear of the second gear set engages only a first gear of the first gear set, to a second position wherein a second gear of the second gear set engages only a second gear of the first gear set, whereby mutually exclusive first and second speeds are selected, the first speed being a high-speed, low-torque speed, and the second speed being a low-speed, high-torque speed, wherein the first and second driven gears, and the receiver, include a continuous keyway; and a key mounted on the second shaft engages the continuous keyway.

\* \* \* \* \*